United States Patent [19]

Hickey

[11] Patent Number: 5,398,692

[45] Date of Patent: * Mar. 21, 1995

[54] COMBINATION ESOPHAGEAL CATHETER FOR THE MEASUREMENT OF ATRIAL PRESSURE

[75] Inventor: Donald D. Hickey, Buffalo, N.Y.

[73] Assignee: The Research Foundation of State University of New York, Albany, N.Y.

[*] Notice: The portion of the term of this patent subsequent to Sep. 17, 2008 has been disclaimed.

[21] Appl. No.: 114,775

[22] Filed: Aug. 31, 1993

Related U.S. Application Data

[63] Continuation of Ser. No. 980,460, Nov. 23, 1992, Pat. No. 5,263,485, which is a continuation-in-part of Ser. No. 717,854, Jun. 25, 1991, Pat. No. 5,181,517, which is a continuation-in-part of Ser. No. 409,041, Sep. 18, 1989, Pat. No. 5,048,532.

[51] Int. Cl.⁶ .............................................. A61B 5/02
[52] U.S. Cl. .................................. 128/673; 128/672; 128/675; 128/687; 128/780; 604/96
[58] Field of Search ................. 128/780, 671, 672, 3, 128/675, 687; 604/96

[56] References Cited

U.S. PATENT DOCUMENTS

| | | | |
|---|---|---|---|
| 4,134,402 | 1/1979 | Mahurkar | 128/214 |
| 4,214,593 | 7/1980 | Imbruce et al. | 128/748 |
| 4,379,460 | 4/1983 | Judell | 128/671 |
| 4,409,986 | 10/1983 | Apple et al. | 128/715 |
| 4,502,490 | 3/1985 | Evans et al. | 128/780 |
| 4,517,984 | 5/1985 | Perlin | 128/642 |
| 4,706,688 | 11/1987 | Micheal et al. | 128/785 |
| 4,729,384 | 8/1988 | Bazenet | 128/691 |
| 4,850,969 | 7/1989 | Jackson | 604/96 |
| 5,048,532 | 9/1991 | Hickey | 128/780 |
| 5,181,517 | 1/1993 | Hickey | 128/780 |
| 5,191,892 | 3/1993 | Blikken | 128/715 |
| 5,263,485 | 11/1993 | Hickey | 128/673 |
| 5,269,775 | 12/1993 | Bodickey | 604/96 |

FOREIGN PATENT DOCUMENTS

1069826 9/1982 U.S.S.R. ......................... 604/96

OTHER PUBLICATIONS

A. J. Gordon et al, "Left Atrial Pulmonary Capillary" and Esophageal Balloon Pressure Tracings in Mitral Valve Disease, Brit. Heart J. 18:327–340, 1956.
(List Continued on Next Page.)

Primary Examiner—Lee S. Cohen
Assistant Examiner—Robert L. Nasser, Jr.
Attorney, Agent, or Firm—Hodgson, Russ, Andrews, Woods & Goodyear

[57] ABSTRACT

Non-invasive apparatus and method for obtaining a quantitative determination of mean left atrial pressure or otherwise obtaining a quantitative determination of a left atrial pressure value. A balloon is inserted by means of a catheter into the esophagus and positioned adjacent the left atrium. The balloon is gradually inflated. A tracing of mean balloon pressure is obtained as the balloon is inflated. In addition, a tracing of balloon pressure on a steady baseline and with low frequency oscillations due to respiration filtered out is obtained whereby the tracing represents balloon pressure oscillations effected by left atrial pressure. In accordance with the oscillometric principle the mean balloon pressure is measured at the time when the amplitude of the balloon pressure oscillations effected by the left atrial pressure is at a peak. This mean balloon pressure is indicative of approximate mean left atrial pressure. Mean left atrial transmural pressure may be determined by subtracting therefrom the mean esophageal pressure as measured at a position in the esophagus where it is unaffected by the heart. The catheter includes a naso-gastric tube and is passed centrally of the balloon whereby the balloon surrounds the catheter so that contact between the balloon and the esophageal wall is not obstructed for greater reliability of mean left atrial pressure determinations. The catheter may also include an esophageal stethoscope and/or an esophageal temperature sensor.

2 Claims, 8 Drawing Sheets

OTHER PUBLICATIONS

"We'll meet your needs.", Teleflex Medical/Fluoroplastics, Incorporated, Tall Pines Park, Jaffrey N.H. 03452.

Brown, *A Study of the Esophageal Lead in Clinical Electrocardiography*, American Heart J., vol. 12, No. 1, Jul., 1936, pp. 1–45.

Oblath and Karpman, *The Normal Esophageal Lead Electrocardiogram*, American Heart J., vol. 41, 1951, pp. 369–381.

Arborelius et al, *Hemodynamic Changes in Man During Immersion with Head Above Water*, Aerospace Medicine, Jun., 1972, pp. 592–598.

Lategola and Rahn, *A Self-Guiding Catheter for Cardiac and Pulmonary Arterial Catheterization and Occlusion*, 84 Proc. Soc. Exp. Biol. Med. 667–668 (1953).

Swan, Ganz, Forrester, Marcus, Diamond and Chonette, *Catheterization of the Heart in Man With Use of a Flow-Directed Balloon-Tipped Catheter*, 283:9 The New England J. Med. 447 (1970).

Murray, *Complications of Invasive Monitoring*, 15:2 Medical Instrumentation 85 at p. 89 (Mar.–Apr. 1981).

Robin, *Death by Pulmonary Artery Flow-Directed Catheter (editorial), Time for a Moratorium?*, 92:4 Chest 727 (Oct. 1987).

H. R. Anderson and P. Pless, Trans-Esophageal Pacing, 6 page 674 (Jul.–Aug. 1983).

R. P. Lasser and L. Loewe, *Characteristic Pressure Pulses Recorded with an Esophageal Balloon in Experimental Mitral Insufficiency in Dogs*, Proc. Soc. Experimental Biol. Med. 77:798 (1951).

R. P. Lasser and L. Loewe, *Esophageal Pressure Pulse Patterns (Esophageal Piezocardiogram)*, Am. Heart J. 44:531 (1952).

A. C. Taquini, *The Esophageal Pulse Under Normal and Abnormal Conditions*, Am. Heart J. 20:2 (1940).

M. Zoob, *The Esophageal Pulse in Mitral Valve Disease*, Brit. Heart J. 16:39 (1954).

Robin, *The Cult of the Swan-Ganz Catheter, Overuse and Abuse of Pulmonary Flow Catheters*, 103:3 Annals of Internal Medicine 445 (Sep./1985).

Rowley, Clubb, Smith and Cabin, *Right-Sided Infective Endocarditis as a Consequence of Flow-Directed Pulmonary-Artery Catheterization*, 311:18 The New England J. Med. 1152 (Nov. 1, 1984).

J. M. Gore et al., *Handbook of Hemodynamic Monitoring*, 3 (1985).

Gore et al., *A Community-Wide Assessment of the Use of Pulmonary Artery Catheters in Patients with Acute Myocardial Infarction*, 92:4 Chest 712–(Oct. 1987).

Baker et al., "Oesophageal Multipurpose Monitoring Probe", Anaesthia, 1983, vol. 38, pp. 892–897.

Fig. 4.
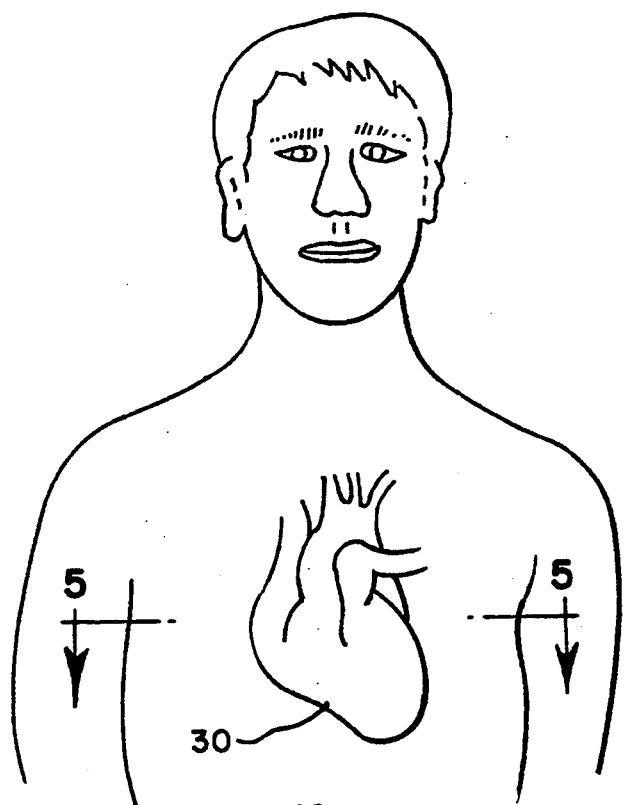
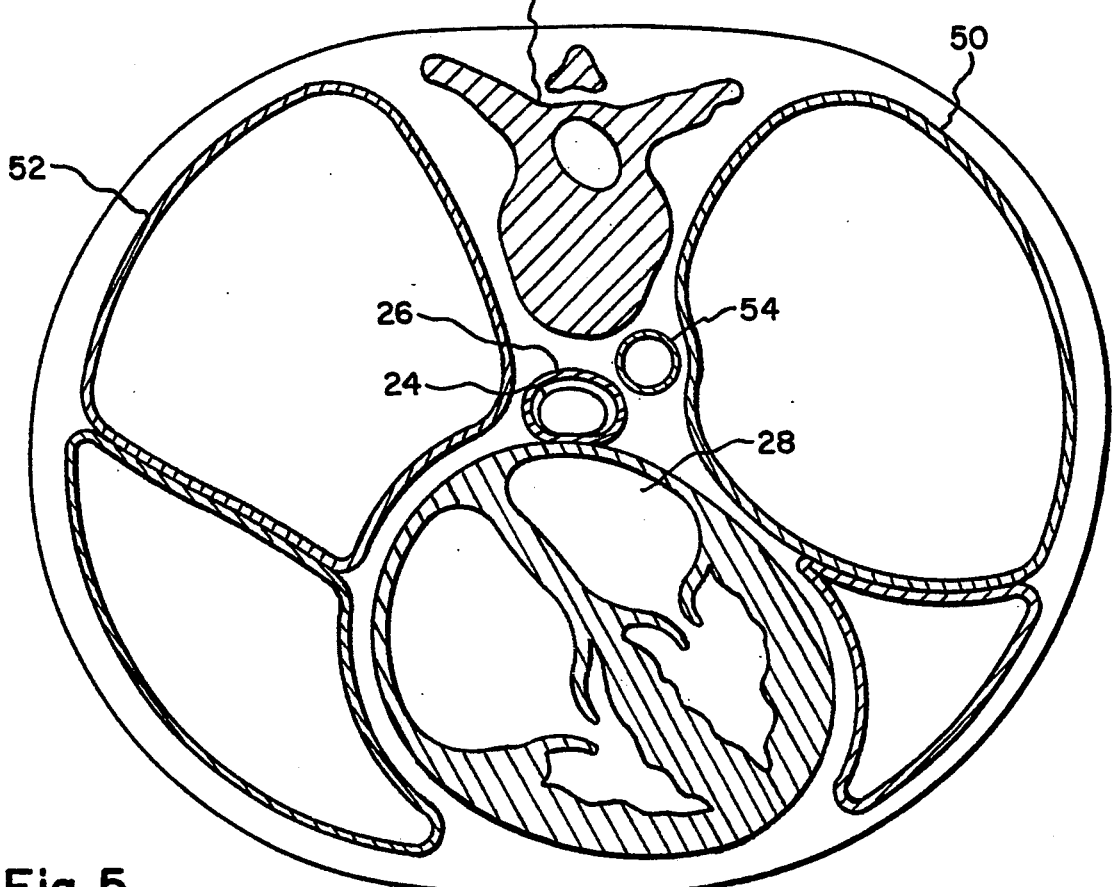
Fig. 5.

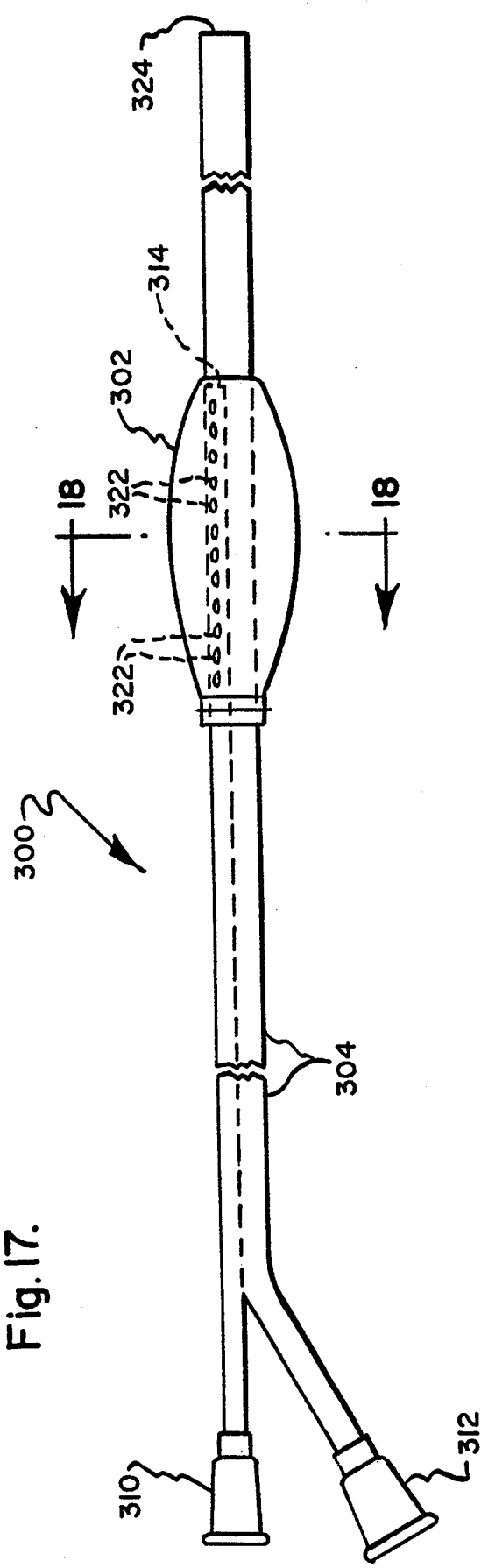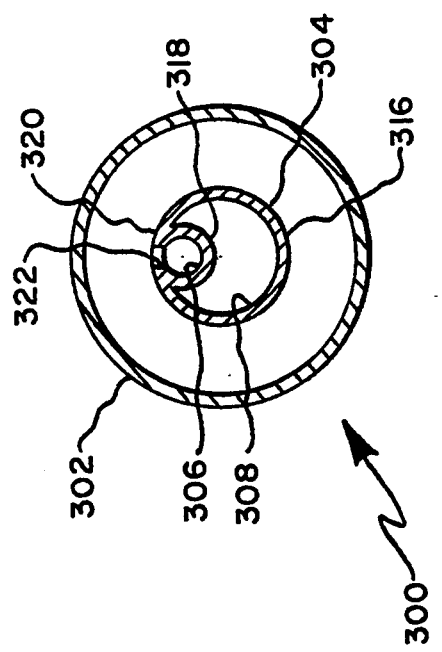

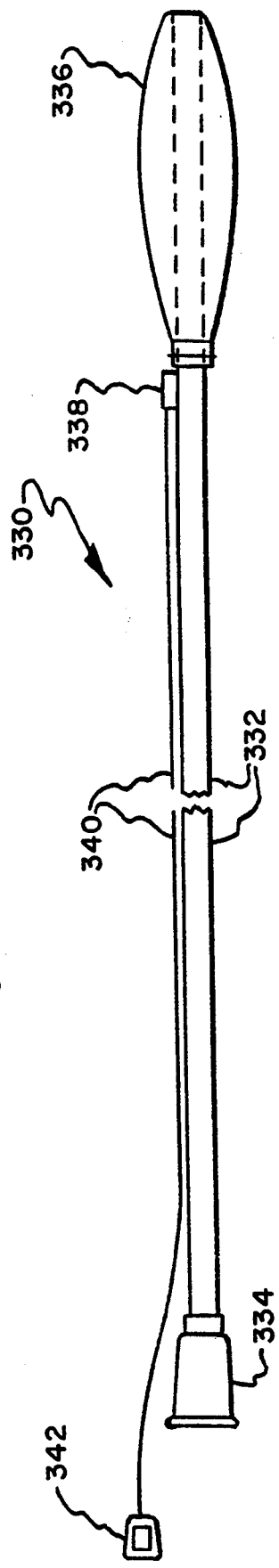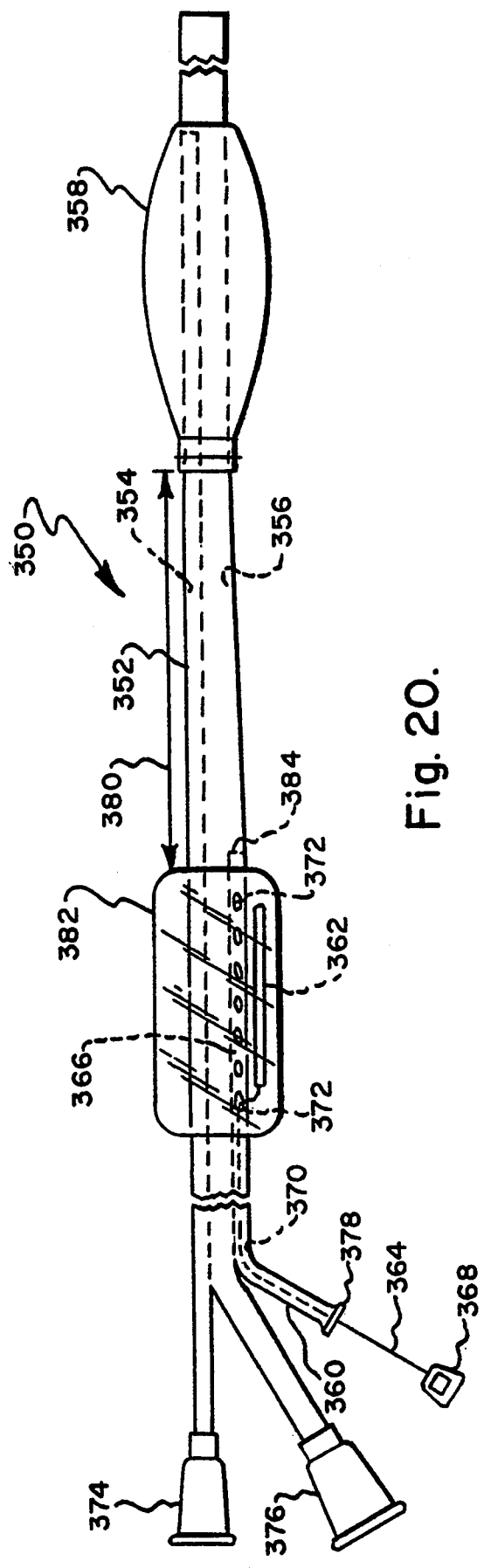
Fig. 19.
Fig. 20.

COMBINATION ESOPHAGEAL CATHETER FOR THE MEASUREMENT OF ATRIAL PRESSURE

This is a continuation of application Ser. No. 07/980,460, filed Nov. 23, 1992 (now U.S. Pat. No. 5,263,485), which is a continuation-in-part of application Ser. No. 07/717,854, filed Jun. 25, 1991 (now U.S. Pat. No. 5,181,517), which is a continuation-in-part of application Ser. No. 07/409,041, filed Sep. 18, 1989 (now U.S. Pat. No. 5,048,532). The disclosures thereof are hereby incorporated herein by reference.

TECHNICAL FIELD

The present invention relates generally to the measurement of blood pressure and, more specifically, to obtaining quantitative pressure values for determining mean left atrial blood pressure as well as other left atrial pressures and pressures associated therewith.

BACKGROUND ART

Ever since the English scientist Stephen Hales first measured the blood pressure by observing the blood rise in a tube inserted in an artery of a horse in 1733, scientists and physicians have sought better ways to measure blood pressure in people.

An instrument in common use for indirectly measuring blood pressure is a sphygmomanometer, which comprises an inflatable cuff which wraps around the upper arm above the elbow, a rubber bulb to inflate the cuff, and a device to measure the levels of pressure. It is well known that if the cuff is inflated to above systolic pressure, then slowly decompressed, oscillations corresponding to the heart rate will appear in the cuff pressure beginning somewhat above systolic pressure. These oscillations typically reach a maximum amplitude and then diminish until they are lost. The French physiologist, E. J. Marey, who discovered this phenomenon in 1876, reasoned that the peak amplitude of oscillation occurred close to mean arterial pressure. This hypothesis was confirmed by later investigators, and various methods of blood pressure determination based on the "oscillometric principle" were subsequently developed.

In 1905, Dr. N. S. Korotkoff proposed an auscultatory method of determining blood pressure. In this method, an arm cuff is inflated until it stops the circulation of blood beyond the cuff. Thereafter, a stethoscope is used to listen to the artery just distal to the sleeve. Korotkoff hypothesized that the first sounds correspond to maximum pressure whereas minimum pressure occurred when the sounds disappeared. Later laboratory and clinical studies confirmed the accuracy of the auscultatory method, which eventually became universally adopted in clinical medicine.

The above techniques have heretofore been considered to provide insufficiently precise measurements for adequate management of cardiac pressures in critically ill patients. It has also not been possible to non-invasively determine left ventricular preload, which heretofore has been determined invasively by measuring the mean left atrial pressure or the pulmonary capillary wedge pressure.

In 1953, Lategola and Rahn demonstrated the efficacy of a flow directed pulmonary artery catheter for the direct measurement of pulmonary artery pressure. Lategola and Rahn, *A Self-Guiding Catheter for Cardiac and Pulmonary Arterial Catheterization and Occlusion,* 84 Proc. Soc. Exp. Biol. Med. 667-668 (1953). In 1970, Swan, Ganz, and associates reported use of a flow-directed catheter in humans and further refined it for clinical use and for the direct measurement of pulmonary capillary wedge pressure. Swan, Ganz, Forrester, Marcus, Diamond, and Chonette, *Catheterization of the Heart in Man With Use of a Flow-Directed Balloon-Tipped Catheter,* 283:9 The New England J. Med. 447 (1970). At present, this catheter is an invaluable aid in the management of critically ill patients with pulmonary and cardiac disease, and the pulmonary wedge pressure (as an estimation of left ventricular filling pressure or preload) is the standard of reference for intravascular volume management.

Numerous potential indications for pulmonary artery catheterization are now accepted. For example, catheterization is widely used in the evaluation and management of patients with acute myocardial infarction, for patients in shock when the cause is not readily apparent, in the recognition of hypovolemia, and in the treatment of patients suffering respiratory failure with persistent hypoexemia, of uncertain cause. Catheterization is especially useful in assessing cardiac function in surgical patients, both pre-, intra-, and postoperatively. Since 1970, the ability to measure pulmonary capillary wedge pressure and cardiac output with the flow-directed catheter has resulted in the development of bedside hemodynamic monitoring, a procedure now performed daily in most hospitals in the United States. J. M. Gore et al., *Handbook of Hemodynamic Monitoring,* 3 (1985). Since the introduction of the Swan-Ganz catheter in 1970, it is reported that several million pulmonary catheters have been placed in patients with acute myocardial infarction. Gore et al., 92:4 Chest, 712 (October 1987).

Despite the widespread use of the pulmonary artery flow-directed catheter, the procedure is not without drawbacks. Complications that may arise from use of the catheter include pulmonary artery thrombosis or embolus, knotting of the catheter, rupture of the balloon and/or of a pulmonary artery, pulmonary hemorrhage, pneumothorax, hemothorax, right atrial thrombosis, sepsis, internal jugular stenosis or thrombosis, atrial and. ventricular arrhythmias, electromechanical dissociation, right-sided endocardial lesions, and right-sided endocardial infection. Robin, *The Cult of the Swan-Ganz Catheter, Overuse and Abuse of Pulmonary Flow Catheters,* 103:3 Annals of Internal Medicine 445 (September 1985). In recent years, the safety and efficacy of pulmonary artery catheterization has become a subject of increased scrutiny and concern. One study suggests that flow-directed pulmonary artery catheterization may predispose patients to the development of right-sided endocarditis. Rowley, Clubb, Smith, and Cabin, *Right-Sided Infective Endocarditis as a Consequence of Flow-Directed Pulmonary-Artery Catheterization,* 311:18 The New England J. Med. 1152 (Nov. 1, 1984). The medical literature abounds with articles addressing the numerous medical complications associated with pulmonary artery catheterization. See, e.g., Murray, *Complications of Invasive Monitoring,* 15:2 Medical Instrumentation 85 at p. 89, March-April 1981, which lists various references related thereto. Perhaps the most serious allegation to date is that complications associated with the use of the pulmonary artery catheter in patients with acute myocardial infarction have resulted in an unusually and unacceptably high mortality rate. Robin, *Death by Pulmonary Artery Flow-Directed Catheter, Time for a Moratorium?* (editorial), 92:4 Chest 727 (October 1987).

In addition to the safety concerns, there is a relatively high monetary cost of critical care invasive monitoring, which cost may be minimized by the availability of a non-invasive procedure where indicated. Thus, a need has existed for a non-invasive and less costly improved method for accurately measuring blood pressure in the left atrium in people.

Invasive hemodynamic measurement nevertheless remains an important and feasible adjunct to clinical practice. Successful monitoring permits accurate determination of the state of the diseased heart and provides guidance for treatment and intervention to alter the course of a variety of diseases. It is recognized that modern Swan-Ganz catheters allow for the measurement of cardiac output, oxygen consumption, continuous mixed venous oxygen saturation, and cardiac pacemaking, and that many critically ill patients will require this degree of sophisticated monitoring. Nevertheless, given the knowledge of mean left atrial pressure alone, there are numerous patients who could be safely managed in intermediate care units or on regular nursing floors. Certain patients undergoing general anesthesia could also benefit from less invasive monitoring of mean left atrial pressures. Furthermore, a less invasive technique for the measurement of mean left atrial pressure could be used to rationally screen patients to determine whether or not they would benefit from Swan-Ganz catheterization; otherwise, monitoring of mean left atrial pressure by such a less invasive technique may suffice to manage the patient outside the intensive care setting.

Thus, a long-felt need exists for a non-invasive method to accurately determine mean left atrial pressure. This is a primary underlying objective of the present invention.

An esophageal catheter with a balloon having an inflated length and diameter of 3.1 cm. and positioned adjacent the left atrium has been used in an attempt to provide the shape of the curve of left atrial pressure. See Gordon et al, *Left Atrial, "Pulmonary Capillary", and Esophageal Balloon Pressure Tracings in Mitral Valve Disease*, British Heart J., 18: 327-340, 1956.

A concern when attempting to pick up left atrial pressure waves using balloon tipped esophageal catheters is the problem of insuring that the balloon is properly positioned behind the left atrium. In connection with the placing of electrodes for trans-esophageal heart pacing, it has been suggested that a positioning balloon may be inserted on the distal end of an esophageal catheter to anchor the catheter in the stomach. Since the distance between the left atrium and the stomach (gastro-esophageal junction) is relatively constant in an adult, the pacing electrodes could then be affixed to the catheter at this distance proximal to the stomach balloon. See Andersen et al, *Trans-Esophageal Pacing*, PACE, Vol. 4, July-August, 1983, p. 674-679. However, this process is not suitable for use with non-adults since the gastro-esophageal junction to left atrial distance will not be constant but will vary for neonates and children. It has also been suggested, in connection with observing the esophageal pulse in mitral valve disease, that an electrode may be used to position an esophageal balloon behind the left atrium by attaching it to the catheter just above the balloon to measure the esophageal electrocardiogram from behind the left atrium. See Zoob, *The Oesophageal Pulse in Mitral Valve Disease*, British Heart J., Vol. 16, 1954, pp. 39-48. Also see Brown, *A Study of the Esophageal Lead in Clinical Electrocardiography*, American Heart J., Vol. 12, No. 1, July, 1936, pp. 1-45; and Oblath and Karpman, *The Normal Esophageal Lead Electrocardiogram*, American Heart J., Vol. 41, 1951, pp. 369-381.

In order to record left atrial events, Gordon et al suggests, at page 330, that the esophageal balloon to be positioned adjacent the left atrium must be relatively small, "otherwise the tracings will be distorted by pressure or volume changes taking place at other than the desired left atrial level" and that it was "usually necessary to suspend respiration while the records were being made."

However, Gordon did not provide pressure measurement and, indeed, stated that his system was incapable of obtaining left atrial pressure values. Thus, Gordon et al states, at page 330, that "no attempt was made to measure absolute pressures from these tracings, as the amplitude of the pressure pulse is a function of the elasticity of the system, the amount of fluid in the balloon and the initial pressure within it, as well as the intra-atrial pressure." As again indicated at page 338 of Gordon et al, one of the drawbacks of the Gordon et al system is the inability to obtain absolute left atrial pressure values. That was more than 30 years ago.

It is an object of the present invention to non-invasively obtain quantitative pressure measurements to determine a person's mean left atrial pressure safely, accurately, and reliably.

It is another object of the present invention to obtain such measurements economically and easily.

It is a further object of the present invention to provide a method for determining a person's mean left atrial pressure which may be administered by a non-physician.

It is yet another object of the present invention to provide a naso-gastric tube in combination with an esophageal catheter for determining mean left atrial pressure so as not to interfere with the determination of mean left atrial pressure.

It is still another object of the present invention to provide an esophageal stethoscope in combination with the catheter.

It is another object of the present invention to provide an esophageal temperature measurement device in combination with the catheter.

SUMMARY OF THE INVENTION

In order to non-invasively determine a person's mean left atrial pressure safely, accurately, and reliably, in accordance with the present invention a balloon is inserted into the person's esophagus and positioned adjacent the left atrium and inflated, and the mean balloon pressure is measured when the amplitude of balloon pressure oscillations effected by the left atrial pressure is at a peak. This peak amplitude is indicative of resonating of the balloon pressure at a pressure effected by the person's mean left atrial pressure, in accordance with the oscillometric principle. This pressure is thus determinative approximately of mean left atrial pressure. The mean left atrial transmural pressure may be determined by subtracting therefrom the pleural pressure, i.e., the pressure on the outside of the heart. It is envisioned that further refinements of this method may lead to the ability to determine other left atrial pressure values such as diastolic and systolic left atrial pressures or other pressures associated therewith.

In order to provide a naso-gastric tube in combination with a catheter containing such a balloon so that the contact between the balloon and the esophageal wall is not obstructed, in accordance with the present invention the naso-gastric tube is passed centrally of the balloon so that the balloon surrounds the tube. The catheter may also include an esophageal stethoscope and/or an esophageal temperature sensing means.

The above and other objects, features, and advantages of the present invention will be apparent in the following Best Mode for Carrying Out the Invention when read in conjunction with the accompanying drawings in which like reference numerals denote the same or similar parts throughout the several views.

BRIEF DESCRIPTION OF THE DRAWINGS

FIG. 4 is a front sectional view of the human body illustrating the position of the heart.

FIG. 5 is a top sectional view of the human body, taken along lines 5—5 of FIG. 4, at the level of the seventh thoracic vertebra and with the balloon of FIG. 1 in the esophagus.

FIG. 17 is a view similar to that of FIG. 1 of a naso-gastric tube in combination with a catheter for determining mean left atrial pressure in accordance with the present invention.

FIG. 18 is a sectional view of the catheter of FIG. 17 taken along lines 18—18 thereof.

FIG. 19 is a view similar to that of FIG. 1 of a thermistor for sensing esophageal temperature in combination with a catheter for determining mean left atrial pressure.

FIG. 20 is a view similar to that of FIG. 1 of the catheter of FIG. 17 also in combination with an esophageal stethoscope and a temperature sensing device.

BEST MODE FOR CARRYING OUT THE INVENTION

Figure 1:
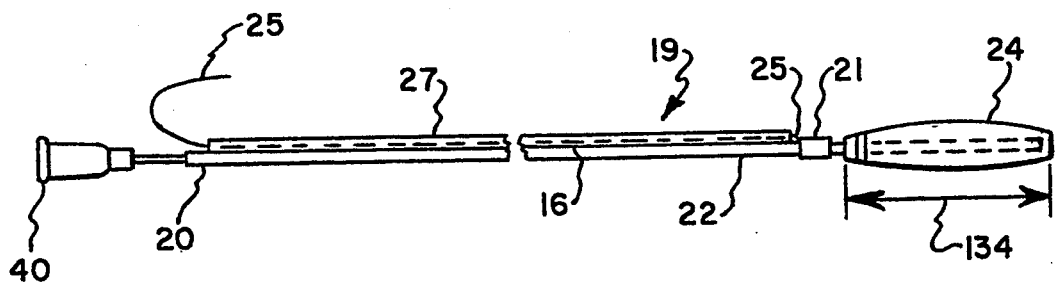
FIG. 1 is a side view of a combination of a balloon-containing catheter and an electrode-containing catheter in accordance with the present invention with the balloon inflated.
Figure 2:
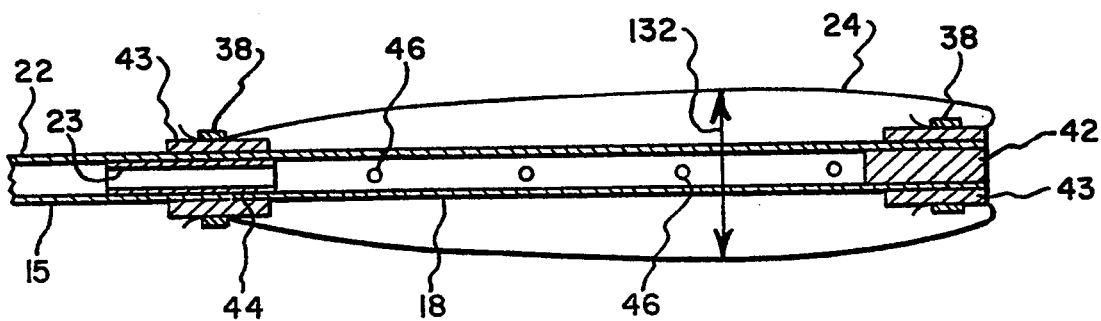
FIG. 2 is an enlarged side sectional view of the balloon of FIG. 1.

Referring to FIGS. 1 and 2, there is illustrated generally at 19 catheter apparatus including a hollow catheter 20 comprising a length of flexible tubing 22 having a bore or lumen 23 and on one end of which is attached a balloon 24 for flow communication with the lumen 23 for pressurization of the balloon and for sensing the pressure thereof. An electrode 21 may be positioned just above the balloon 24 for obtaining an esophageal electrocardiogram and an electrical lead 25, within a second catheter 27, provided thereto, as will be discussed in greater detail hereinafter.

Figure 3:
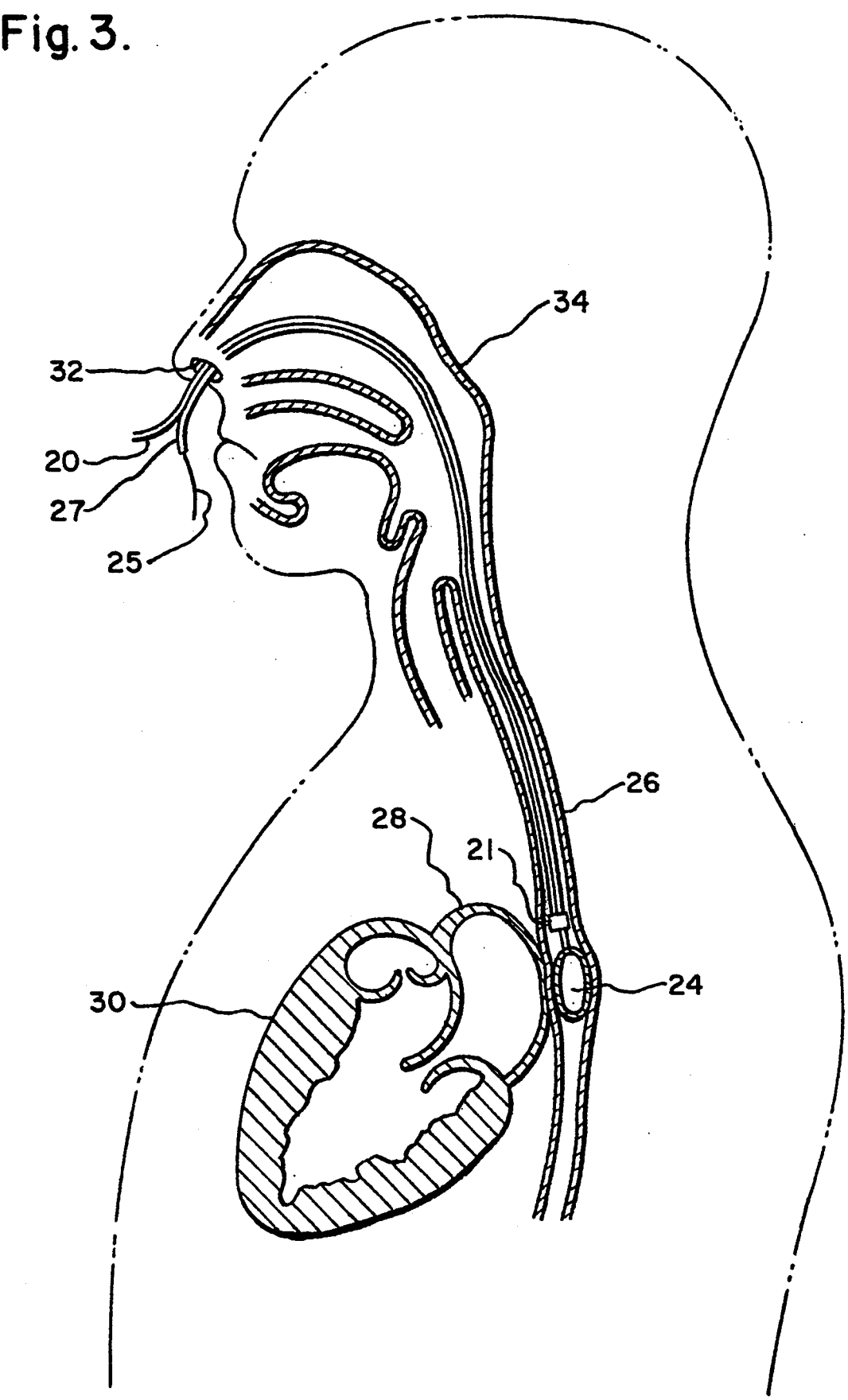
FIG. 3 is a partial left lateral sectional view of the human body taken along the mid-sagittal plane and showing the balloon of FIG. 1 within the esophagus and adjacent the left atrium of the heart.

Referring to FIG. 3, there is illustrated the placement of the balloon 24 within the esophagus 26 of a human body for the purpose of sensing the mean pressure of the left atrium 28 of the heart 30. The catheter 20 is inserted balloon first through nasal passage 32, pharynx 34, then into the esophagus 26. If desired, the balloon may alternatively be inserted through the mouth. As shown in FIG. 3, the outer wall of the left atrium 28 is adjacent and essentially in direct contact with the outer wall of the esophagus 26, and advantage is taken of this relationship to determine mean left atrium pressure by means of the balloon 24 thusly inserted non-invasively into the esophagus 26 and positioned therealong adjacent the left atrium so as to be sufficiently affected thereby to sense left atrium pressure, as will be discussed in greater detail hereinafter.

The tubing 22 may be composed of any suitable flexible, chemically inert, non-toxic material such as polyvinyl chloride for withstanding operating pressures without significant expansion. A preferred tubing is a Tygon ® brand polyvinyl chloride tubing having an inner diameter of approximately 0.050" which is a product of Cole-Parmer Instrument Co., 7425 North Oak Park Avenue, Chicago, Ill. 60648-9930, as shown on page 636 of the Cole-Parmer 1989–90 Catalog. The tubing 22 has a suitable length which may be perhaps 80 cm. The tubing 22 may desirably have markings (not shown) along the length thereof to indicate distance therealong so that the balloon 24 may be initially positioned approximately adjacent the left atrium 28. The tubing may contain a portion 18 which extends over the length of the balloon 24 and a portion 15 which extends from the balloon. Portions 15 and 18 are connected by means of a stainless steel ferrule 44 over which the tubing is press fit. The distal end of the balloon is closing by plugging by a cylindrical plug 42 of stainless steel or the like over which tubing portion 18 is press fit. At each balloon end, a sleeve 43 is fitted over the tubing portion 18 to provide a larger diameter for securing the balloon fabric. Each balloon end is then sealed by surgical thread 38 and/or silicone cement. A plurality of apertures 46 are provided in the tubing (portion 18) wall over a distance from the closed end 42 equal to less than the balloon length to provide flow communication between the tubing 22 and the interior of the balloon 24 for inflating the balloon and for sensing pressure therein. The balloon 24 fits over the tubing portion 18 containing the apertures 46 and is attached to the tubing 22 at end portion 42 and at ferrule or second portion 44 between which portions are the apertures 46, as illustrated in FIG. 2. Pressurization and sensing lines may be attached at the end 40, which is opposite the balloon end 42, as will be discussed in greater detail hereinafter.

However, other suitable means may be used for such attachment. For example, the balloon may be fixed over the end of a catheter the end of which is plugged. The balloon 24 may be constructed of any suitable flexible non-toxic film which can withstand operating pressures without rupture or irreversible deformation. The balloon 24 may have a capacity of perhaps about 2 milliliters. When inflated within the pressure range for measuring mean left atrial pressure, the balloon 24 takes on a generally cylindrical shape, as illustrated in FIGS. 1 and 2. The thickness of the material of which the balloon 24 is made is perhaps about 0.0005". The balloon 24 should function properly in any rotational orientation around the longitudinal catheter axis. The balloon 24 may, for example, be constructed of low density polyethylene film such as Extrel ® SF brand polyethylene film, a product of Exxon Chemical Co., Polymers Group, Division of Exxon Corp., 351 North Oakwood Road, Lake Zurich, Ill. 60047-1562.

Referring to FIGS. 4 and 5, it should be noted that the esophagus 26 is sandwiched between the left atrium 28 and the vertebral column 48 so that when the balloon 24 is positioned adjacent the left atrium 28 the vertebral column 48 acts similarly as an anvil for effective action of the left atrium pressure on the balloon 24 to affect the pressure therein as will be described hereinafter. The esophagus 26 is flanked by the left and right lungs 50 and 52 respectively. The aorta 54 is positioned generally between the esophagus 26 and the left lung 50 and in proximity to the vertebral column 48, as shown in FIG. 5.

Figure 6:
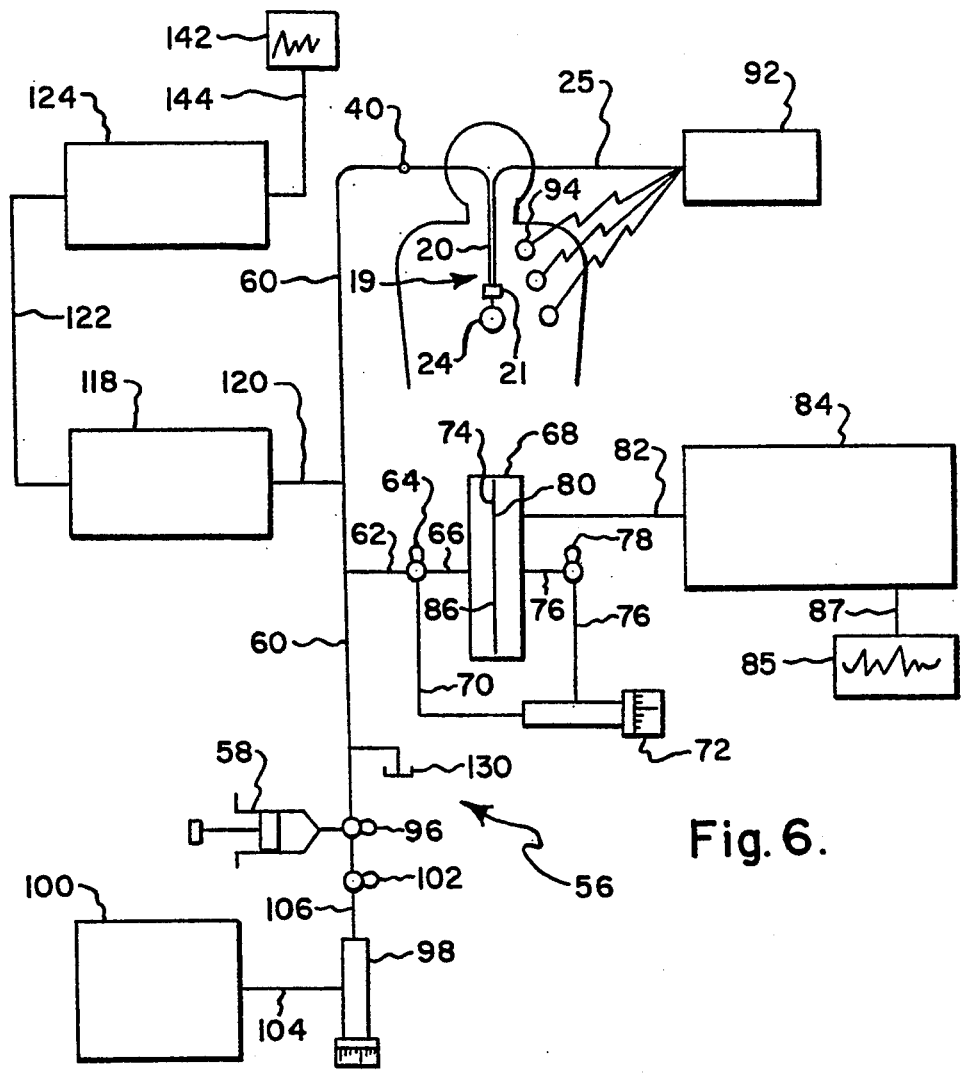
FIG. 6 is a schematic view of apparatus, including the balloon-containing catheter of FIG. 1, which embodies the present invention.

Referring to FIG. 6, there is illustrated generally at 56 apparatus for pressurizing the balloon 24 and for sensing the pressure therein. For the purpose of precisely positioning the balloon 24 adjacent the left atrium 28, the balloon 24 is first statically filled with a predetermined quantity of perhaps 1.4 milliliter of air via syringe 58, with stop cock or valve 96 suitably open for passage of the air therefrom through line 60 to tubing 22 to which line 60 is suitably attached at the end portion 40.

The balloon pressure is transmitted from line 60 through line 62 to four-way stop cock or valve 64 which transmits the pressure through line 66 to one side 74 of the diaphragm 86 of a differential pressure transducer 68 and through line 70 to filter 72. Transducer 68 may, for example, be a Validyne model DP7 differential pressure transducer provided by Validyne Engineering Corp., 8626 Wilbur Avenue, Northridge, Calif. 91324. Pressure from the filter 72 is transmitted through line 76 and stop cock or valve 78 to the other side 80 of the transducer 68. The transducer 68 converts the net pressure signal acting on the diaphragm 86 to an electrical signal which is transmitted through line 82 to a first signal processor 84. Processor 84 may be any suitable conventional electronic signal processing circuit which amplifies and otherwise processes and conditions the electrical signal representations of pressure and communicates these signals to a display means 85 via line 87. Display means 85 may be a digital display, a strip chart recorder, a cathode ray tube, or any other suitable device for displaying or utilizing the signals from processor 84.

The balloon 24 will not only sense atrial pressure but will also record normal peristaltic waves from swallowing as well as pressure excursions from normal breathing. Peristaltic waves are easily distinguished by their high amplitude (up to 100 cm of water) and relative infrequency and can therefore be ignored. Respiratory excursions (typically from −10 to +10 cm of water at frequencies of 0.1 to 0.8 Hertz) can interfere with left atrial pressure wave form and measurement. They are therefore filtered out during signal processing as described hereinafter.

Filter 72 is a low pass mechanical filter such as, for example, a Nupro ® micrometer needle valve connected as shown in FIG. 6, a product of Nupro Company of 4800 East 345th Street, Willoughby, Ohio 44094. The unprocessed signal carrying both the higher frequency cardiac wave form (generally 1.5 to 9.0 Hertz) effected by left atrial pressure and the lower frequency respiratory wave form (generally 0.1 to 0.8 Hertz) goes directly to the first side 74 Of the differential pressure transducer 68 via line 66. An identical signal is also transmitted to the variable control valve 72. By restricting an orifice (not shown) in filter 72, in accordance with principles commonly known to those of ordinary skill in the art to which this invention pertains, the balloon pressure wave is filtered to selectively pass the lower frequency component, which includes respiratory artifact, through line 76 and valve 78 to the other side 80 of the differential transducer 68, and the higher frequency component is excluded. This in effect allows the respiratory artifact arriving almost in phase on both sides of the transducer diaphragm 86 to cancel itself out so that the cardiac wave form is recovered and outputted as an electrical signal through line 82 to the first signal processor 84

Figure 7:
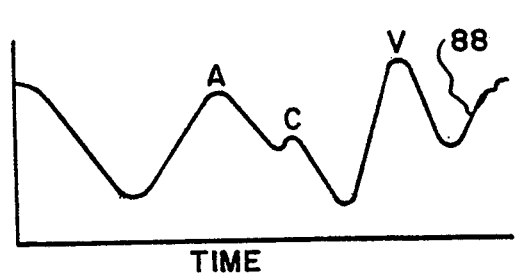
FIG. 7 is a pressure trace of the left atrial pressure during one cardiac cycle as sensed by the balloon of FIG. 1 when adjacent the left atrium.

With the balloon inflated, it is precisely positioned adjacent the left atrium 28 by moving it up or down the esophagus 26 by withdrawing or inserting the catheter 20 at the nose until a typical left atrial pressure wave form, illustrated at 88 in FIG. 7, is seen on the pressure trace from the first signal processor 84. As previously discussed, this wave form 88 comprises the balloon pressure signal with the lower frequency respiratory wave form filtered out. This wave form 88 may be confirmed as being a typical left atrial pressure wave form by comparison with a simultaneous esophageal electrocardiogram, illustrated at 140 in FIG. 8, which is recorded by a conventional electrocardiograph, illustrated at 92 in FIG. 6. Electrocardiogram 140 is obtained by the use of a stainless steel electrode, illustrated at 21, which is suitably attached to the catheter 20 just above the balloon 24. However, the electrode 21 may be otherwise adjacent the balloon 24. For example, an electrode for this purpose could comprise conductive material on the surface of the balloon. An electrical lead 25 is attached to the electrode and extends within a second catheter 27 and to electrocardiograph 92 for transmitting the signals picked up by the electrode 21 for processing therein. The lead 25 may, for example, be silvered 30 AWG wire-wrapping wire provided by OK Industries, 4 Executive Plaza, Yonkers, N.Y. 10701. The catheters 20 and 27 may be held together by suitable securing means such as, for example, cyclohexanone glue 16. Alternatively, a double-lumen catheter of pre-formed polyvinyl chloride may be used. The electrode 21 is preferably in the shape of a ring which encircles catheter tubing 22 so as to insure that it will be suitably positioned without interference by tubing 22 for sensing left atrial electrical activity. In accordance with conventional practice, it may be required that skin electrodes 94 also be hooked-up to the subject. The wave form 140 is characterized by a wave portion (which heralds atrial depolarization) which reaches a high voltage and becomes bi-phasic with a sharp upstroke and shows an intrinsicoid deflection. Thus, points A, C, and V, shown on wave form 88 in FIG. 7, are three essential components of the left atrial pressure wave, and these points are known to correspond to points P, R, and T respectively on the electrocardiogram 140 of FIG. 8 thus confirming that the wave form 88 is a typical left atrial pressure wave form.

When, as the balloon and esophageal electrode are moved up and down the esophagus, a typical left atrial wave form, similar to wave form 88, is sensed on the pressure trace from the first signal processor 84, which indicates that the balloon 24 is suitably positioned adjacent the left atrium 28, the balloon 24 is then fixed in place by applying tape over the catheter 20 and onto the upper lip just beneath the nose. The distinctiveness of this wave form, confirmed by use of electrode 21, may desirably reduce the level of skill required for proper positioning of the balloon. Alternatively, a conventional surface or skin electrocardiogram may be obtained, by use of electrodes 94 on the subject's body and wired to electrocardiograph 92, for comparison with wave form 88 to determine when the balloon is correctly positioned. However, the use of the esophageal electrocardiogram 140 for this purpose is considered preferable since it may provide a more distinctive wave form which is more easily recognized. The use of either the esophageal or skin electrodes for positioning the balloon is advantageously suitable for use with the wide range of body size from premature neonates to adult men.

Figure 16:
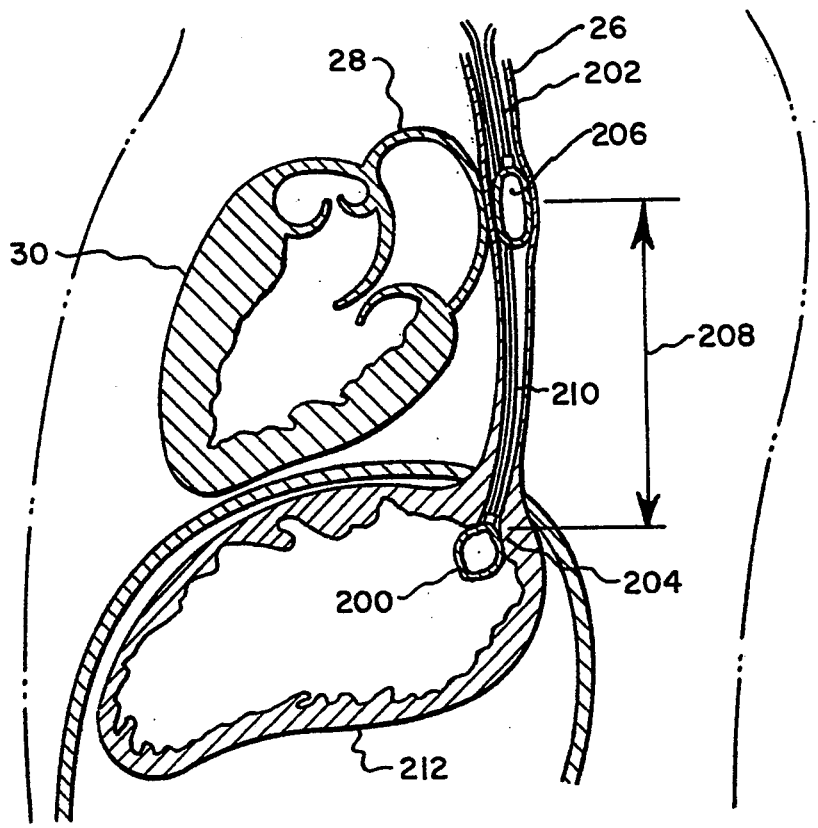
FIG. 16 is a view similar to that of FIG. 3 of an alternative means for sensing position of an esophageal balloon adjacent the left atrium.

Other means for suitably positioning the sensing balloon may alternatively be used. For example, as illustrated in FIG. 16, a positioning balloon 200 may be positioned on a catheter 210 to contact the esophago-gastric junction 204 at the stomach 212 of an adult and a sensing balloon 206 positioned on a separate catheter 202 (since the positioning balloon 200 must be inflated before inflation of the sensing balloon 206 is begun) and at a distance from the positioning balloon 200 which approximates the relatively constant distance, illustrated at 208, in an adult between the esophago-gastric junction 204 and the left atrium 28. This distance 208 is of course relatively constant in adults but not in premature neonates and infants.

As previously discussed, the pressure wave form 88 is insufficient for determining mean left atrial pressure due to its amplitude being a function of the elasticity of the system, the amount of gas in the balloon, and the initial pressure within it, as well as the intra-atrial pressure and the surrounding tissue pressure. With the balloon 24 precisely positioned, processing can begin for accurately and non-invasively determining the mean left atrial pressure, as discussed hereinafter.

After proper placement has been accomplished, sensing balloon 24 is initially evacuated to perhaps −10 to −12 cm of water pressure, less than the minimum expected pressure to be measured, using syringe 58, with the stop cock 96 open thereto. This purges the system of any gas, prior to beginning a measurement, to insure consistency, accuracy, and reliability of pressure measurements. The system is similarly also purged of any residual gases between measurements.

After the balloon 24 has been properly placed adjacent the left atrium 28 and evacuated, it is gradually inflated with air or another suitable inert gas such as, for example, nitrogen gas or a suitable liquid such as, for example, water for the purpose of determining mean left atrial pressure as hereinafter described. The use of a liquid may provide enhanced gain. If a liquid is used, it may be provided to line 60 by means of a liquid-filled syringe to which is attached a suitable mechanical or hydraulic pressurization device. The use of air may simplify the equipment and its use and may therefore be preferred for this purpose. A source of air under a sufficient pressure such as, for example, 40 psig for inflating the balloon 24 is illustrated at 100. With stop cocks or valves 96 and 102 opened to connect the metering gas supply valve 98 with the line 60 and with syringe 58 closed to line 60 by valve 96, the gas from source 100 is routed through line 104 to the metering valve 98 where it is released to line 106 and through stop cocks 102 and 96 and line 60 to catheter 20 in metered quantity for gradually inflating the balloon 24 As used herein and in the claims, the term "line" unless otherwise specified, is meant to refer to tubing, a catheter, an electrically conductive wire, or other suitable means for transmitting a pressure or electrical signal. Valve 98 is a Nupro® brand micrometer needle valve, a product of Nupro Company of 4800 East 345th Street, Willoughby, Ohio 44094, which is constructed to allow a broad range of near constant flow rates against back pressures to a maximum of about 50 cm water (0.74 psi). It is precalibrated to provide gas flows up to about 4 milliliters per minute on average. Other suitable valves may alternatively be provided. Metering valve 98 is thus opened to provide a suitable gas flow such as a flow of approximately 1.0 milliliter per minute for gradually filling the sensing balloon 24 at a constant rate.

While not wishing to be bound by theory here or elsewhere in this specification, the following is believed to occur as the sensing balloon 24 is pressurized. The gradual filling of the sensing balloon 24 causes the pressure therein to increase at a generally slow steady rate which, in accordance with the theory of the previously discussed oscillometric effect, is affected by the atrial pressure causing oscillations therein as well as by respiratory waves. As the mean balloon pressure approaches the mean left atrial pressure, the atrial pressure oscillations of balloon pressure increase in intensity or amplitude until the balloon pressure resonates maximally, i.e. reaches a peak amplitude, when the mean balloon pressure approximates the mean left atrial pressure. Thereafter, as the mean balloon pressure continues to increase, the amplitude of oscillations due to the atrial pressure decreases. More specifically, the balloon pressure oscillates maximally when its expansion has increased the pressure in the tissue surrounding the left atrium to the point where the mean tissue pressure equals mean left atrial pressure (MLAP). Thus, it may be said that the balloon works best as a pressure transmitter when it is unloaded, i.e., when the mean pressure on both sides of the balloon wall are equal, resulting in the greatest amplitude of balloon pressure oscillations when the mean balloon pressure equals mean left atrial pressure.

Figure 8:
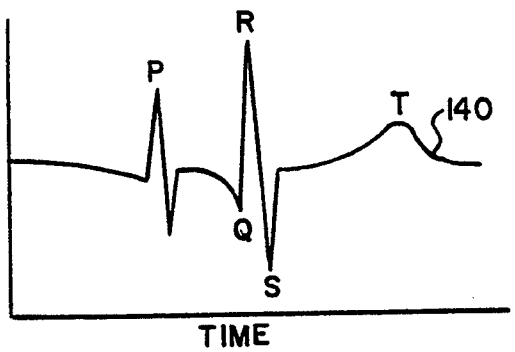
FIG. 8 is a graph of an esophageal electrocardiogram of the left atrium during one cardiac cycle.
Figure 12:
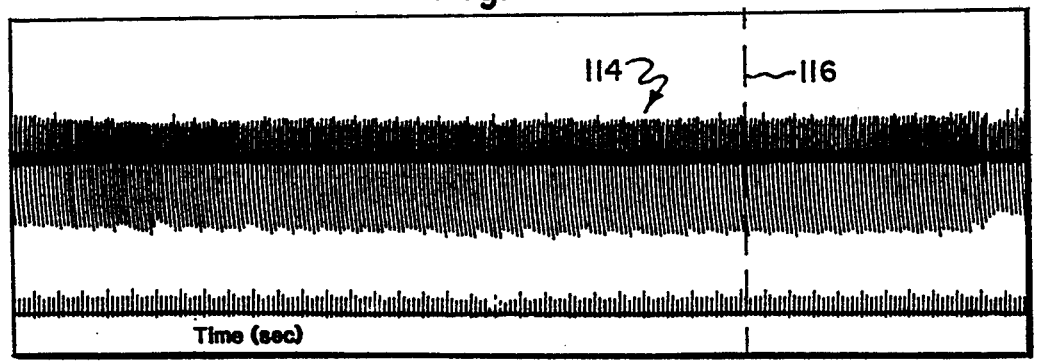
FIG. 12 is a graph of an electrocardiogram taken simultaneously with the pressure traces of FIGS. 9, 10 and 11.

FIGS. 9 to 12 are illustrations of four electronic displays or tracings used to record and display the absolute balloon pressure wave form 108 (FIG. 9), the mean balloon pressure wave form 110 (FIG. 10), the differential signal 112 with added gain from the signal processor 84 (FIG. 11), and a simultaneous electrocardiogram 114 (FIG. 12). Vertical line 116 in each of FIGS. 9 to 12 represents the same point in time. A comparison of the electrocardiograms 140 and 114 in FIGS. 8 and 12 respectively indicates that the time scale for FIGS. 7 and 8 is greatly expanded relative to the time scale for FIGS. 9 to 12, i.e., the wave form 140 in FIG. 8 covers a period of about a second, and a multitude of such waves over a multitude of seconds is shown in FIG. 12.

The absolute balloon pressure wave form 108 is obtained from a suitable transducer 118 connected to line 60 via line 120. The transducer 118 may, for example, be a Cobe CDX III transducer provided by Cobe Laboratories, Inc., 1185 Oak Street, Lakewood, Colo. 80215. The transducer 118 converts the balloon pressure signal in line 120 to an electrical signal which is transmitted through line 122 to second signal processor 124, which is a suitable conventional electronic signal processing circuit which suitably processes and conditions the electrical signal representations of pressure and transmits these signals to a suitable display means 142, which may be similar to display means 85, via line 144. The processor 124 amplifies the signal for display as shown by tracing 108 in FIG. 9. Signal processor 124 also suitably processes the signal, in accordance with principles commonly known to those of ordinary skill in the art to which this invention pertains, to provide an electronic mean thereof as shown by tracing 110 in FIG. 10. The transducer 118 is referenced to one atmosphere of pressure absolute.

It should be recognized that other suitable analog or digital electronic signal processing means can be employed to filter, amplify, compare, and otherwise process the signals. Both pressure transducers 68 and 118 are suitably calibrated against a water manometer prior to use.

A suitable relief valve 130 is provided in line 60 to protect the system 56 and the patient from over-pressurization. The relief valve 130 is set to open at a suitable pressure of perhaps 50 cm of water pressure to vent the tubing and balloon to atmosphere in order to prevent dangerously high pressure such as might cause the balloon to rupture.

The absolute balloon pressure wave form 108 is comprised of low amplitude high frequency oscillations effected by left atrial pressure which are superimposed on high amplitude low frequency respiratory oscillations which are in turn superimposed on the gradual increase in balloon pressure provided by gas supply valve 98. The mean balloon pressure wave form is shown at 110 in FIG. 10. By "mean balloon pressure" is meant, for the purposes of this specification and the claims, the balloon pressure at the mean of each of the high frequency (greater than about 0.8 Hertz) oscillations. Stated another way, the "mean balloon pressure" wave form 110 is the absolute balloon pressure wave form 108 with the high frequency oscillations removed therefrom. When a signal is filtered, waves which are removed therefrom do not appear in the output while those which are passed or extracted do appear in the output. The abrupt slope change indicated at 200 from a fast to a slowed rate of pressure increase is indicative of the equalization of balloon pressure with the surrounding tissue pressure prior to balloon expansion.

The differential signal 112 is provided by the signal processor 84 after low frequency oscillations representing the respiratory artifact are filtered out by the differential pressure transducer 68 so that the left atrial pressure wave form is recovered. In addition, the rising absolute pressure due to the gradual inflation of the balloon 24 (which is treated by the filter 72 similarly as a low frequency oscillation and thus passed to transducer side 80) is also cancelled out by the differential transducer 68 so that the pressure signal 112 processed by signal processor 84 is on a steady base line. The signal 112 is then further filtered electronically, amplified, and displayed by the signal processor 84 on display 85.

Wave form 112 may alternatively be obtained by electronically inverting the mean balloon pressure wave form 110 and adding the inverted wave form to the absolute balloon pressure wave form 108 and amplifying the oscillations obtained.

Figure 13:
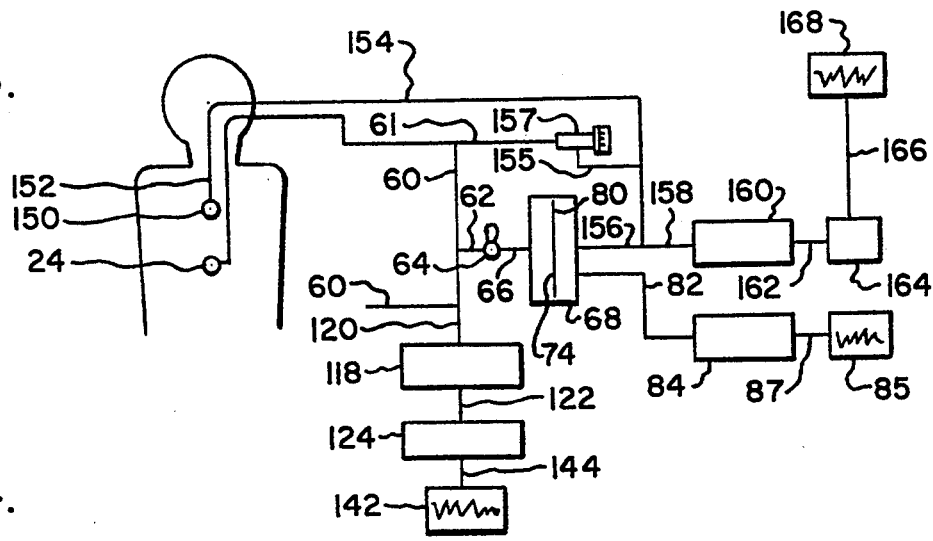
FIG. 13 is a schematic view of an alternative embodiment of the present invention, it being understood that this embodiment is meant to include the portion of apparatus of FIG. 6 which is connected to line 60.

The use of a bias balloon 150 for alternatively eliminating respiratory artifact to obtain signal 112 is illustrated in FIG. 13. The pressure in balloon 24 is transmitted through lines 60, 62, and 66 to one side 74 of differential pressure transducer 68 similarly as illustrated in FIG. 6. This pressure, which is also transmitted through line 120 to transducer 118 and converted to an electrical signal which is processed and displayed on display 142, includes the effects of respiratory artifact as well as atrial pressure. The bias balloon 150, similar to balloon 24 and similarly inserted by means of a catheter 152, which may be similar to catheter 20, may also be pressurized via line 60 as hereinafter discussed. Bias balloon 150 is inserted into the esophagus intermediate the position of the left atrium and the nasal or mouth passage, i.e., perhaps 3 or 4 cm. or more above the position of balloon 24, so that the pressure therein is not affected by left atrial pressure. But bias balloon 150 does sense respiratory artifact, i.e., pressure swings generated by respiration, and therefore may be said to reflect esophageal pressure and thus record the respiration induced fluctuation in esophageal pressure. The bias balloon pressure is transmitted through lines 154 and 156 to the other side 80 of differential pressure transducer 68. Thus, a pressure effected by absolute left atrial pressure plus respiratory artifact is applied to one side 74 of transducer 68, and a pressure effected by respiratory artifact is applied to the other side 80. The difference, representative of left atrial pressure without the respiratory artifact, is outputted as an electrical signal through line 82 to signal processor 84 which transmits a suitably processed signal of the resulting difference wave through line 87 to signal display 85, which may be similar to display 142. One advantage of bias balloon 150 is that its use will eliminate respiratory artifacts regardless of their frequency. If desired, the bias balloon 150 could also be used to independently measure simultaneous esophageal pressure by transmitting the bias balloon pressure from line 154 via line 158 to transducer 160, which may be similar to transducer 118, which converts the pressure to an electrical signal which is then transmitted via line 162 to signal processor 164, which may be similar to processor 124, in which the signal is suitably processed and transmitted via line 166 to display 168, which may be similar to display 142.

Figure 9:
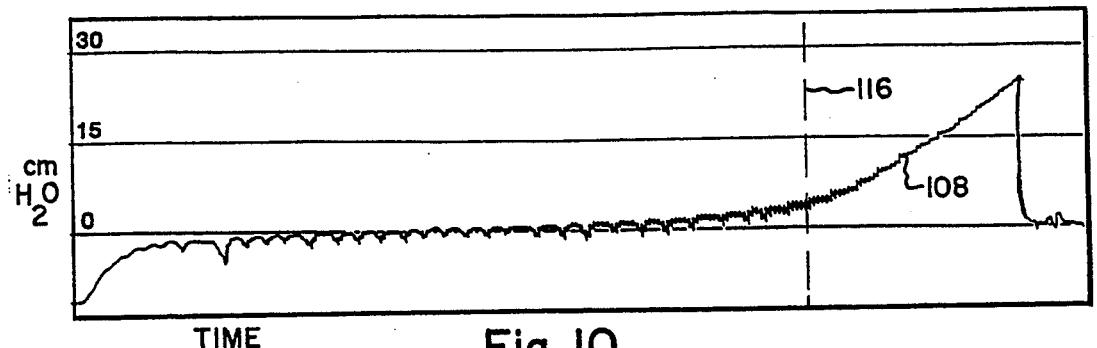
FIG. 9 is a pressure trace of an unfiltered signal of balloon pressure with respiratory and cardiac effected oscillations when the balloon of FIG. 1 is adjacent the left atrium, as the balloon is gradually pressurized.
Figure 10:
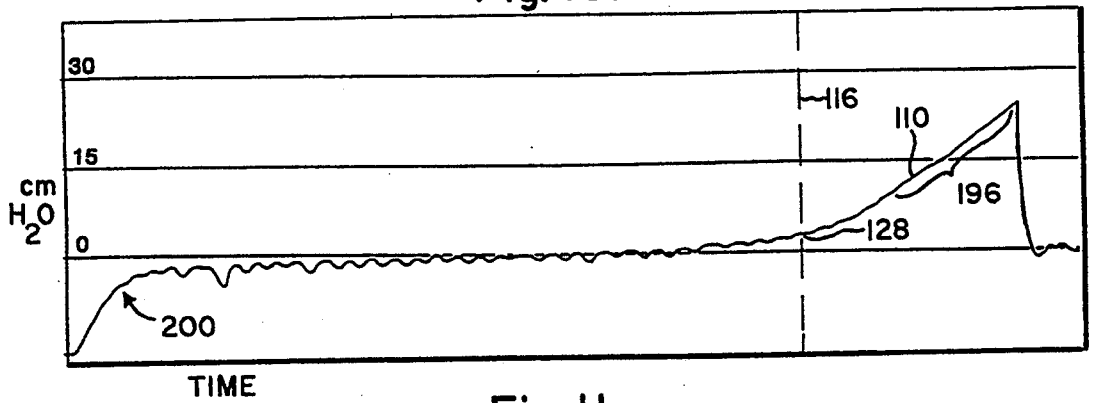
FIG. 10 is a pressure trace of mean balloon pressure for the pressure trace of FIG. 1.
Figure 11:
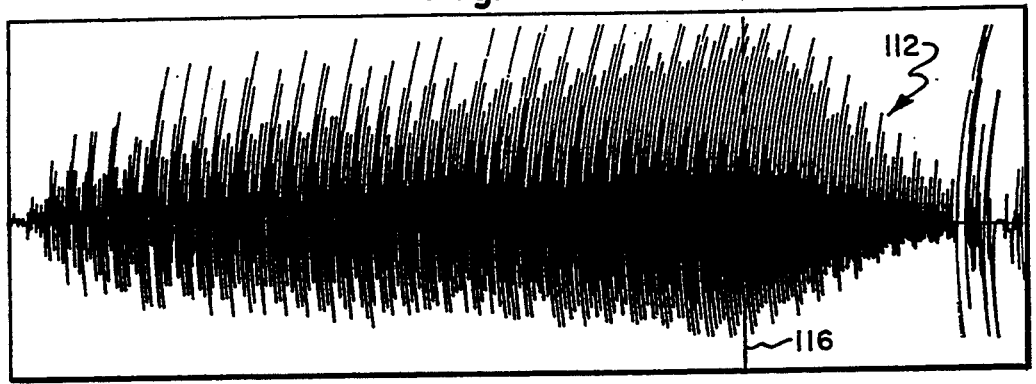
FIG. 11 is a pressure trace of amplified cardiac signal on a steady baseline which signal is derived from the balloon pressure trace of FIG. 9 and covers the same time period as that of FIGS. 9 and 10.

As shown in FIGS. 9 and 10, the low frequency oscillations representative of respiratory artifact decrease in amplitude as the pressure in the balloon 24 increases. In order that the same amplitude of respiratory wave at each point in time may be supplied to both sides of the pressure transducer 68 so that effective cancellation of respiratory artifact may be achieved, balloons 150 and 24 are both connected to gas supply 100 via line 60. Thus, lines 61 and 155 connect line 60 to line 154 for inflation of balloon 150. In order to prevent the cardiac signals from appearing on the bias balloon signal, a suitable low pass filter 157, which may be similar to filter 72, is connected so that line 61 extends from line 60 to input pressure from pressure source 100 to filter 157, and the output of filter 157, with the cardiac waves removed, is transmitted via lines 155 and 154 to balloon 150. In accordance with an alternative embodiment (not shown), two separate gas supplies may be provided for balloons 24 and 150 to prevent signal contamination with suitable pressure transducers and electronic feedback means to automatically maintain the mean pressure in the bias balloon 150 equal to the mean pressure in the sensing balloon 24. In accordance with another alternative embodiment (not shown), two separate gas supplies may be provided with a pressure regulator on the bias balloon side which is referenced to the mean sensing balloon pressure and such that cardiac oscillations are not conducted across the regulator.

It should be understood that other means, for example, analog or digital filtering techniques applied directly to the absolute balloon pressure to remove low frequency artifacts such as from respiration or peristalsis may be used for deriving wave form 112 from the absolute balloon pressure, and such other means are meant to come within the scope of the present invention.

The wave form 112 is thus an oscillating signal of varying amplitude on a steady baseline. These oscillations, derived from absolute balloon pressure, are in response to the driving pressure of the left atrium.

By noting the peak resonant amplitude of the wave form 112 (FIG. 11) and comparing it to the simultaneous mean balloon pressure 110 (FIG. 10), the mean left atrial pressure can be determined. Thus, in accordance with the oscillometric principle, the mean balloon pressure approximates the mean left atrial pressure when the oscillations of wave form 112 are at a peak, i.e., the peak or highest amplitude oscillations in the wave form 112 occur at the time 116 the balloon pressure is equal to mean left atrial pressure. The mean left atrial pressure is thus determined from the example of FIGS. 9 to 12 to be a pressure, illustrated at 128, of about 3 cm water.

It should be recognized that mean left atrial pressure may alternatively be approximated by reference to the absolute balloon pressure wave form 108. Thus, the relatively small amplitude of the high frequency oscillations on wave form 108 would permit one to estimate the mean balloon pressure from which an estimation of mean left atrial pressure may be obtained.

It should be understood that it is not essential to the present invention that the wave forms in FIGS. 9 to 12 be actually obtained in graph or tracing form. For example, an electronic peak detector may alternatively be used to sense the maximum or peak amplitude, and associated electronics may then determine and display the corresponding mean left atrial pressure in accordance with principles commonly known to those of ordinary skill in the art to which this invention pertains.

The relaxed diameter of the normal adult esophagus is about 2.5 cm. The inflated balloon diameter should be less than this in order to avoid stretching the esophagus since, if this were to happen, not all of the balloon pressure would be applied to the left atrial wall with the result that the balloon pressure at peak oscillation would be higher than the mean left atrial pressure. In addition, if the balloon is too large, its inflation may trigger secondary peristalsis. On the other hand, if the inflated balloon diameter is too small, it will not be able to exert adequate pressure against the left atrium during inflation, nor will it have optimal contact area to optimize pulse transmission. The balloon length should be adequate to provide optimal longitudinal contact with the left atrium and pulmonary veins in which the mean pressure equals mean left atrial pressure, but should not extend too far beyond the left atrium where it could pick up pressure artifacts from the aorta or lower esophageal sphincter. In accordance with the above requirements, for use in adults, the balloon 24 preferably has an inflated diameter, illustrated at 132 in FIG. 2, Which is between about 0.9 and 1.5 cm and an inflated length, illustrated at 134 in FIG. 1, which is between about 3.0 and 4.0 cm. More preferably, the balloon 24 has an inflated diameter 132 of about 1 cm and an inflated length 134 of about 3.5 cm providing a volume of about 2 milliliters. This diameter still allows the vertebral column to serve as an anvil since the esophagus is normally collapsed. For children and neonates the above sizes will be suitably reduced.

Figure 14:
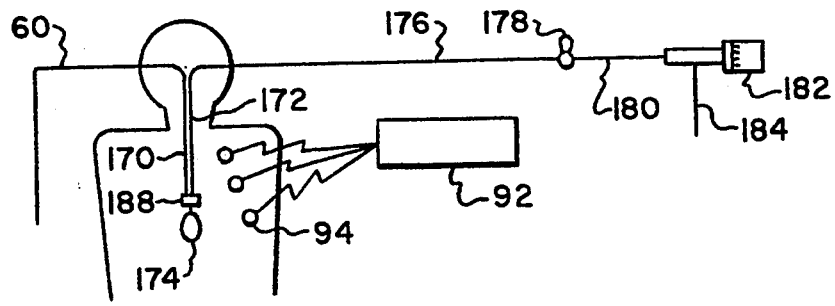
FIG. 14 is a schematic view of an alternative embodiment of the present invention, it being understood that this embodiment is meant to include the portion of apparatus of FIG. 6 which is connected to line 60.

Maximum oscillation of balloon pressure may coincidently occur just before the balloon reaches its full volume after which the balloon pressure may rise very sharply, as indicated at 196 in FIG. 10. Sometimes this sharp rise may obscure the point of maximum balloon oscillation. In order to allow better control of balloon pressure filling for smoother balloon inflation near the point of maximum oscillation, in accordance with a preferred embodiment, illustrated in FIGS. 14 and 15, a balloon with an exhaust line for exhausting the balloon outside the body is used to slow such a rapid pressure rise. In this embodiment, a pair of catheters 170 and 172 containing lumens 171 and 173 respectively are attached to esophageal balloon 174. Catheter 170 is attached to line 60. Though not shown in FIG. 14 for ease of illustration, the equipment attached to line 60 in FIG. 6 should also be understood to be attached to line 60 in FIG. 14. Catheter 172 is connected via line 176 to a four-way stopcock 178 or other suitable valve and subsequently via line 180 to a Nupro controlled exhaust valve 182 which exhausts through line 184 to atmosphere. Exhaust valve 182 may be of any suitable type such as, for example, one which is similar to control valve 98.

Figure 15:
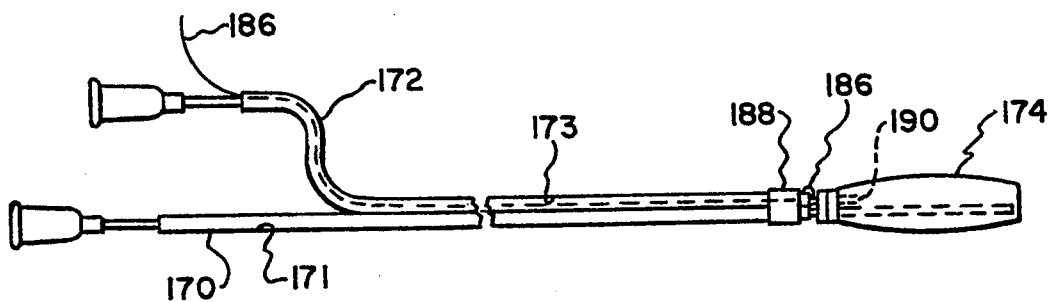
FIG. 15 is a view similar to that of FIG. 1 of the catheter apparatus of FIG. 14.

As discussed previously with respect to the embodiment of FIG. 6, when an exhaust valve is not used the control valve 98 is set at a constant flow rate and then left alone to gradually fill the balloon. However, with the stopcock 178 open to connect the exhaust valve 182 to the balloon 174, the exhaust valve 182 is set to a position which is determined by experience, and which can be determined by one of ordinary skill in the art to which this invention pertains without undue experimentation, and control valve 98 is used for balloon pressure control. The balloon 174 is pressurized by steadily opening the control valve 98 and using the exhaust valve 182, which is set at the fixed setting and left alone, to provide back pressure. The control valve 98 is thus continuously opened to increase the flow through the balloon 174 with the pressure gradually rising. At some point, in accordance with the oscillometric principle the balloon oscillates maximally, as effected by left atrial pressure, after which the oscillations decrease as the balloon pressure increases further. The exhaust valve 182 is provided to achieve finer supply gas control so that the peak of oscillations may be more precisely determined. Thus, as the pressure in the balloon 174 increases, it is believed that the flow through the exhaust valve 182 increases, thus slowing and stabilizing the pressure rise, without affecting the relative amplitudes of oscillations effected by left atrial pressure whereby the peak in such oscillations may still occur at the same balloon pressure value from which mean left atrial pressure can be determined. An esophageal electrode wire 186 for an electrode 188, which may be similar to electrode 21, is routed through the exhaust line catheter 172 to thereby alleviate the need for a separate catheter for the wire 186. As seen in FIG. 15, the catheter 172 suitably extends into the interior of balloon 174 and has an open end 190 for receiving exhaust. By closing the stopcock 178, the embodiment of FIG. 14 can, if desired, be reverted for use without the exhaust line, similarly as discussed with respect to the embodiment of FIG. 6.

If desired, lumens 171 and 173 may be provided within a single catheter. In accordance with another alternative embodiment, a single lumen catheter may be provided with a side port which has a vent valve that could provide some back pressure during filling but which would attenuate the abrupt pressure rise when the balloon reaches its maximum volume. Yet another means for attenuating this abrupt pressure rise may be to throttle the flow-control valve as maximum balloon volume is reached so that filling toward the end stages is slowed.

In certain body positions such as supine and semi-recumbent, the heart weight bears on the esophagus. In other body positions such as standing, sitting, lying on the side, or prone, the heart weight would not bear on the esophagus. It is presently believed that the pressure effect of heart weight per se against the esophagus has little if any effect on the peak balloon oscillation pressure irregardless of the body position of the patient. However, in order to insure a measurement of peak balloon oscillation pressure uninfluenced by heart weight, it is preferred that the determination of mean left atrial pressure, as hereinbefore described, be made while the patient is positioned standing, sitting, lying on the side, prone, or in any other position wherein the heart weight does not bear on the esophagus.

A physiologically and medically important pressure, the mean lest atrial transmural pressure, can also be determined with information available from the catheter. This pressure is the difference between the mean left atrial pressure and the pleural pressure (the pressure of the tissue immediately surrounding the heart). It is important to know this transmural pressure because it can influence the degree to which fluid will leave the pulmonary capillaries and enter the lung tissue, causing pulmonary edema or "wet lungs".

The pleural pressure can be determined by measuring the mean esophageal pressure in the esophagus at a location above and away from the heart, i.e., at least about 3 or 4 cm above the heart, such as to be unaffected by pressure in the heart, using principles commonly known to those of ordinary skill in the art to which this invention pertains.

The mean esophageal pressure can be determined by moving the sensing balloon away from under the heart after peak oscillation measurement or by the use of a second balloon-tipped catheter. For example, bias balloon 150 of FIG. 13 may be used to obtain esophageal pressure, uninfluenced by heart weight, which is determined by measuring the balloon pressure at a slope change, which may be similar to slope change 200, from a fast to a slowed rate of pressure increase indicative of equalization of balloon pressure with the surrounding tissue pressure, i.e., mean esophageal pressure, prior to balloon expansion. Alternatively, the mean esophageal pressure may be determined by evacuating balloon 150, then adding a small volume of gas (slightly greater than the dead space volume of the catheter and connecting tubing), and taking the mean of the resulting esophageal pressure wave form.

The method and apparatus of the present invention may be used for providing precise determination of mean left atrial pressure for patients connected to respirators. However, when a patient is connected to a breathing machine which uses positive end expiratory pressure (PEEP), the patient's pulmonary capillary wedge pressure (PCWP) and mean left atrial pressure (MLAP) may be elevated as a result, since all intrathoracic structures are exposed to varying degrees to this pressure. Since mean esophageal pressure reflects intra-pleural pressure (a good measure of the pressure environment in the chest), the mean esophageal pressure will provide a measure of the effect of PEEP on thoracic structures. Thus, the mean left atrial transmural pressure, as provided by the catheter, provides an excellent means to understand the physiologic and clinical impact of PEEP on the heart and lungs since it takes into account simultaneous pressure changes induced in both the left atrium and the esophagus by the imposition of PEEP.

Using the process of the present invention, as illustrated in FIG. 6 and using a surface electrocardiogram for positioning the balloon 24, average mean left atrial pressure measurements were obtained for two healthy adults with the catheter in these persons sitting upright dry or immersed to the neck in thermoneutral water. The results were as follows:

| Subject | Average Mean Left Atrial Pressure | |
| --- | --- | --- |
|  | Dry | Immersed |
| No. 1 | −3.5 cm H$_2$O | +13 cm H$_2$O |
| No. 2 | 0 cm H$_2$O | +15 cm H$_2$O |

A paper entitled *Hemodynamic Changes in Man during Immersion with the Head Above Water*, Aerospace Medicine, June, 1972, pp 592–598, shows data from subjects with intracardiac monitoring subjected to similar conditions. While the paper indicates that mean left atrial pressures were not measured, both mean right atrial and pulmonary artery diastolic pressures were measured. These pressures are known to be roughly similar to mean left atrial pressures in young healthy adults. As indicated in Table 1, p. 594, of the paper, the average values were:

|  | Dry | Immersed |
| --- | --- | --- |
| Mean right atrial pressure | −2 mm Hg | +16 mm Hg |
| Pulmonary artery diastolic pressure | +3 mm Hg | +20 mm Hg |

Note that 1 mm Hg=1.3 cm H$_2$O. These results indicate that the values of average mean left atrial pressure obtained, in accordance with the present invention, are within the expected range, i.e., both studies showed a 2 percent increase in pressures during immersion when referenced to one atmosphere in the corresponding units of measurement: 1000 cm H$_2$O of 760 mm Hg. Later testing by Applicant has continued to confirm that the values obtained when measuring balloon pressure when the amplitude of balloon pressure oscillations effected by the left atrial pressure when the balloon is adjacent the left atrium is at a peak in accordance with the present invention may be used as indicative of mean left atrial pressure.

Without wishing to be bound by theory, it is believed that the balloon best transmits not only pressures acting on it but also sound when unloaded. Thus, the amplitude of heart sounds transmitted through the balloon and tubing is believed to be greatest when the mean balloon pressure equals the mean left atrial pressure so that the balloon is unloaded. Accordingly, in accordance with another embodiment of the present invention, the balloon pressure may be measured when the amplitude (intensity) of sound waves (sound pressure level) transmitted by the balloon and tubing is at a peak as an indication of mean left atrial pressure. Thus, a condenser-type or other suitable microphone (not shown) may be suitably positioned in a three-way stop cock in an entrance to the tubing to pick up these sounds, which may then be filtered with a high pass filter to remove extraneous frequencies less than perhaps about 30 Hertz. Alternatively, a band pass filter may be used. Such a microphone may, for example, be an Archer PC-mount condenser microphone element marketed by Radio Shack, a division of Tandy Corp., of Fort Worth, Tex. under its catalog no. 270-090.

Since the air pressure in the balloon tubing is oscillating and steadily increasing during balloon inflation, the microphone must undergo simultaneous pressure equilibration if it is to work properly. Normally this is done for other applications with a small pressure equilibration hole that allows slow pressure equilibration in response to slow barometric pressure changes. However, in the balloon tubing of the present invention, pressure changes occur too quickly for satisfactory pressure equilibration and a larger hole, while providing for rapid equilibration, could destroy microphone function. Therefore, the microphone must be tuned to allow low frequency pressure changes to equilibrate across the body of the microphone while preventing the much higher sound frequencies from equilibrating. One means to accomplish this is to connect a selected length of the correct diameter micro-bore tubing to the microphone housing, which then acts as a low pass filter. For example, for the Radio Shack microphone discussed above, the micro-bore tubing may have a length of perhaps about 6 inches and an inner diameter of perhaps about 0.015 inch. The tubing may, for example, be PE20 low density polyethylene microbore tubing manufactured by Clay Adams Intramedic and available from Thomas Scientific of 99 High Hill Road, P.O. Box 99, Swedesboro, N.J. 08085 as featured in the Thomas Scientific catalog of 1991-1992 on page 1364 (catalog no. 9565-S16) The tuned microphone then equilibrates rapidly to the high amplitude low frequency ambient pressure changes but does not equilibrate to very low amplitude, high frequency sound components. Therefore, it can pick up the sound components as desired. This would be the case for condenser, dynamic, and piezo-electric microphones.

During treatment of patients, it may be desirable to insert in the esophagus instruments other than the previously discussed balloon-containing catheter, and it may be necessary to insert such additional instruments to extend beyond the position of the balloon. For example, it may be necessary to insert a naso-gastric tube for providing fluids to or removing fluids from the stomach for feeding or suction. However, by being disposed to lie between the balloon and the esophageal wall, such a tube may undesirably interfere with pressure transmission between the esophageal wall and the balloon for determining mean left atrial pressure.

In order to prevent such an additional instrument from interfering with the balloon-esophagus interface, in accordance with the present invention a naso-gastric tube or other elongate means extending beyond the balloon is caused to pass centrally of the balloon so that the balloon surrounds the tube. Thus, referring to FIGS. 17 and 18, there is generally illustrated at 300 a catheter apparatus which includes a balloon 302, similar to balloon 24, for sensing left atrial pressure as previously discussed with respect to balloon 24. The balloon 302 is suitably attached, similarly as described for balloon 24, to a double-lumen tube 304, i.e., a tube having a pair of passages 306 and 308 each being separated from the other so that fluid in one cannot enter the other. Passage 306 provides flow communication with the balloon 302, and passage 308 provides flow communication with the stomach thereby serving as a naso-gastric tube. The term "naso-gastric tube" is meant to include tubes or passage means inserted through the mouth as well as nose, i.e., providing open communication between the lumen of the stomach and the outside of the patient's body. Separate inlets 310 and 312 are provided for the passages 306 and 308 respectively.

The passage 306 passes through the length of the balloon 302 and terminates in a closed end, illustrated at 314, which is suitably sealed such as by heat seal or epoxy. If desired for ease of manufacture or other reasons, passage 306 may extend beyond the end of the balloon. As shown in FIG. 18, the tube 304 has a circular wall 316 to allow ease of sealing attachment of the balloon 302 at its ends thereto. The tube 304 is preferably extruded to provide a tubular wall 318, which defines passage 306, contained within wall 316 and sharing with wall 316, at least over a portion of the length of the balloon but preferably generally over the length of the passage 306 for ease of manufacture, a common wall portion circumferentially which is illustrated at 320. The space between the walls 316 and 318 defines passage 308. A plurality of apertures 322 are provided in the common wall portion 320 to provide flow communication between the passage 306 and the interior of the balloon 302. As shown in FIG. 18, the apertures 322, being in the common wall portion 320 and thus extending into passage 306, do not extend into passage 308 and thus do not provide communication between the passage 308 and the balloon.

The passage 308.extends beyond sealed end 314 and terminates at open end 324 to serve as a naso-gastric tube. Since the nasogastric passage extends centrally through the balloon, it does not lie between the balloon and the esophageal wall to interfere with pressure transmission therebetween.

The double-lumen tube 304 may be manufactured using principles commonly known to those of ordinary skill in the art to which this invention pertains. For example, tube 304 may be extruded fluoropolymer tubing such as provided by Teleflex Incorporated of Jaffrey, N.H., which incorporates in its tubing a variety of equal or unequal lumen passages and diameters to the requirements of its customers. It should be understood that tube 304 may be constructed to provide more than one passage extending beyond the balloon 302 and that the tube 304 may have other configurations. For example, an alternative embodiment of tube 304 may comprise two tubes bonded together.

Referring to FIG. 19, there is illustrated a catheter 330 having a length of tubing 332, including an inlet end 334, to which tubing other end a balloon 336 is attached for determining mean left atrial pressure, similarly as described for catheter 19 of FIG. 1. In order to measure esophageal temperature, a suitable temperature sensor such as a thermistor, illustrated at 338, is suitably embedded in the tubing wall and/or adhesively or otherwise suitably attached thereto. The thermistor is preferably positioned near the level of the atrium, i.e., adjacent the balloon 336. A line 340 extends along the tubing length, and may be suitably attached thereto at spaced intervals, to transmit signals indicative of esophageal temperature conventional apparatus, illustrated generally at 342, for processing the signals and displaying the esophageal temperature. It should be understood that thermistor 338 may be similarly provided in combination with catheter 300 of FIGS. 17 and 18.

Referring to FIG. 20, in accordance with another embodiment of the present invention there is shown generally at 350 a multi-lumen catheter, including a circular tube 352 having passages 354 and 356, similar to passages 306 and 308 respectively, and having suitably attached thereto a balloon 358, similar to balloon 302, for determining mean left atrial pressure, as previously described. Passages 354 and 356 have inlets 374 and 376 respectively. In combination therewith is also provided an esophageal stethoscope sound transmission passage 360, which comprises a third lumen 370 which has an end portion 378 for attachment to a conventional stethoscope and extends along the catheter length to a closed end 384. The lumen end portion 366 terminating in end 384 has a plurality of apertures, illustrated at 372, in a common wall portion circumferentially of the tube 352 and passage 370 to provide communication between passage 370 and the outside of the tube 352 for transmission of heart sounds. The closed end 384 and apertures 372 may be provided similarly as the closed end 314 and apertures 322 are provided for the catheter 300 of FIGS. 17 and 18. End portion 366 and apertures 372 may extend over a length of perhaps about 2 to 3 inches.

A protective pouch 382 composed of a suitable sound transmissable translucent plastic material is suitably secured to and surroundingly engages the end portion 366, containing the apertures 372, of the circular catheter tube 352. If, for example, the pouch 382 is constructed to have a plurality of sound-transmitting apertures, they are suitably protectively coated in a conventional manner to prevent entry of esophageal fluids without unduly interfering with sound transmission.

The stethoscope passage 360 may incorporate a temperature sensor such as a thermistor 362 contained within pouch 382 and a line 364 connected to and extending from sensor 362 through one of the apertures 372 and through passage 370 to a conventional signal processing and display means, illustrated at 368.

A suitable esophageal stethoscope sound transmitting tube with type T thermocouple temperature sensor, which can be adapted for use with the catheter tube 352 in accordance with principles commonly known to those of ordinary skill in the art to which this invention pertains, is marketed by Respiratory Support Products, Inc. of Irvine, Calif. under its catalog no. ESTC-18.

The lumen end portion 366 is spaced from the balloon 358 a distance, illustrated at 380, which is equal to between about 1 and 6 cms, preferably about 3 cms, so as not to interfere with balloon 358 while being in a suitable position for picking up heart sounds. As previously discussed, this spacing is preferably such that the thermistor 362 is positioned as close to the balloon 358 as possible without undue interference by the stethoscope with the balloon.

It should be understood that while the present invention has been described in detail herein, the invention can be embodied otherwise without departing from the principles thereof. Such other embodiments are meant to come within the scope of the present invention as defined by the appended claims.

What is claimed is:

1. Apparatus comprising a catheter which includes a balloon and is insertable into an esophagus for positioning said balloon adjacent the left atrium, means for inflating said balloon, means for Sensing the balloon pressure and providing a balloon pressure signal, and means for filtering the balloon pressure signal to remove oscillations thereof having a frequency less than about 0.8 Hertz, whereby a wave form of oscillations effected by left atrial pressure free of oscillations having a frequency less than about 0.8 Hertz may be obtained for obtaining a quantitative determination of mean left atrial pressure.

2. A method of obtaining a quantitative determination of mean left artial pressure comprising the steps of:
   a. inserting a catheter including a balloon into an esophagus;
   b. positioning the balloon adjacent the left atrium;
   c. inflating the balloon;
   d. sensing the balloon pressure and providing a balloon pressure signal; and
   e. filtering the balloon pressure signal to remove oscillations thereof having a frequency less than about 0.8 Hertz whereby a wave form of oscillations effected by left atrial pressure free of oscillations having a frequency less than about 0.8 Hertz may be obtained.

* * * * *